United States Patent [19]

Roos et al.

[11] Patent Number: 4,472,549

[45] Date of Patent: Sep. 18, 1984

[54] CYCLIC ACETALS OF DIOLS, THEIR PRODUCTION OF THEIR USE AS NON-DISCOLORING ANTIOZONANTS

[75] Inventors: Ernst Roos, Odenthal; Werner Jeblick, Leverkusen; Lothar Ruetz, Dormagen, all of Fed. Rep. of Germany

[73] Assignee: Bayer Aktiengesellschaft, Leverkusen, Fed. Rep. of Germany

[21] Appl. No.: 407,747

[22] Filed: Aug. 13, 1982

[30] Foreign Application Priority Data

Aug. 25, 1981 [DE] Fed. Rep. of Germany ....... 3133567

[51] Int. Cl.³ .............................................. C08K 5/15
[52] U.S. Cl. .................................................. 524/108
[58] Field of Search ................ 260/757, 800; 524/108, 524/487, 488; 549/333; 568/820, 823

[56] References Cited

U.S. PATENT DOCUMENTS

| | | | |
|---|---|---|---|
| 2,472,147 | 6/1949 | Dermer | 549/333 |
| 3,032,520 | 5/1962 | Shaw | 260/757 |
| 3,233,009 | 2/1966 | Carlick et al. | 568/820 |
| 3,278,607 | 10/1966 | Lussling | 568/823 |
| 3,423,348 | 1/1969 | Eigenfeld et al. | 524/487 |
| 3,682,969 | 8/1972 | Batzer et al. | 549/333 |
| 4,088,630 | 5/1978 | Roos et al. | 524/108 |

Primary Examiner—John Kight
Assistant Examiner—Kriellion Morgan
Attorney, Agent, or Firm—Connolly and Hutz

[57] ABSTRACT

Condensation products of a diol with aldehydes corresponding to the following formula:

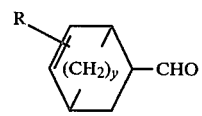

in which R represents hydrogen or methyl, the methyl group being in the 3- and/or 4-position, and Y represents the number 0 or 1, a process for its production characterized in that diols are reacted with aldehyde compounds in known manner, and its use as an antiozonant for rubber.

1 Claim, No Drawings

CYCLIC ACETALS OF DIOLS, THEIR PRODUCTION OF THEIR USE AS NON-DISCOLORING ANTIOZONANTS

This invention relates to condensation products of diols with tetrahydro-Δ³-benzaldehydes or endomethylene tetrahydro-Δ³-benzaldehydes.

The invention also relates to a process for producing the condensation products, to their use as antiozonants in natural and/or synthetic rubber and to the rubbers stabilised with the anti-ozonants.

The following alcohols are mentioned as diols:

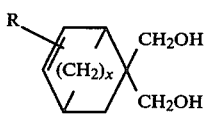

In this formula, R represents hydrogen or methyl (the methyl group may be in the 3- and/or 4-position) and X has a value of 0 or 1. Where X=0, therefore, the alcohols assume the following formula:

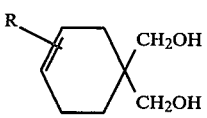

Tetrahydro-Δ³-benzaldehydes and endomethylene tetrahydro-Δ³-benzaldehydes are compounds corresponding to the following formula:

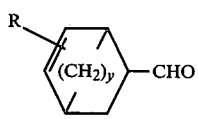

in which R represents hydrogen or methyl (the methyl group may be in the 3- or 4-position) and Y assumes a value of 0 or 1. Where Y=0, therefore, the aldehydes assume the following formula:

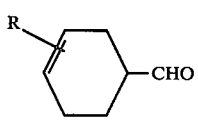

The following are examples of suitable aldehydes of the type in question: tetrahydro-Δ³-benzaldehyde, 3-methyl-tetrahydro-Δ³-benzaldehyde, 4-methyltetrahydro-Δ³-benzaldehyde, 3,4-dimethyltetrahydro-Δ³-benzaldehyde, 2,5-endomethylene-tetrahydro-Δ³-benzaldehyde, 2,5-endomethylene-3-methyl tetrahydro-Δ³-benzaldhyde, 2,5-endomethylene-4-methyl tetrahydro-Δ³-benzaldehyde, 2,5-endomethylene-3,4-dimethyltetrahydro-Δ³-benzaldehyde.

Accordingly, the compounds according to the invention may be represented by the following formula:

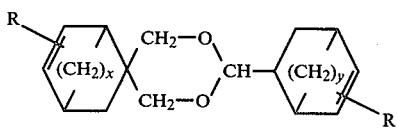

The following are preferred compounds according to the invention

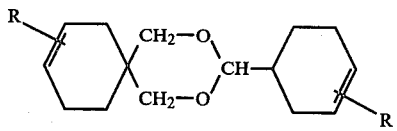

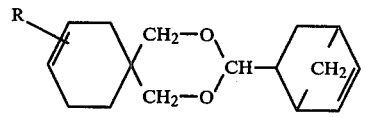

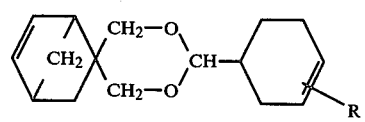

The condensation of the above-mentioned diols with the tetrahydro-Δ³-benzaldehydes may be carried out by methods analogous to those commonly used for the acetalation of alcohols with aldehydes.

The polyhydroxyl compound is generally reacted with the aldehyde preferably in the presence of catalytic quantities of an acid dehydration catalyst at temperatures in the range of from 0° to 200° C. and preferably at temperatures in the range of from 20° to 120° C., 1 mole of aldehyde being used per mole of alcohol.

The reaction may be carried out in the presence or absence of solvents. Suitable solvents are both polar solvents such as water, methanol, ethanol or dioxane, and apolar solvents, such as petrol, benzene or toluene. Where water-immiscible solvents are used, they may optionally be used for azeotropically distilling the water formed during the condensation reaction.

Suitable acid dehydration catalysts are HCl, $ZnCl_2$, $H_2SO_4$, benzene sulphonic acid, naphthalene sulphonic acid or p-toluene sulphonic acid, p-toluene sulphonic acid being preferred.

The catalysts are preferably used in a quantity of from 0.05 to 5% by weight and more preferably in a quantity of from 0.1 to 1% by weight, based on the aldehyde.

The condensation products according to the invention may be added to natural and/or synthetic rubbers to stabilise them against degradation by ozone.

The condensation products according to the invention may readily be dispersed in rubber mixtures and may be used in conjunction with the usual rubber chemicals (for example vulcanisation accelerators, vulcanising agents, antiagers, plasticizers, fillers, waxes, dyes, etc.) without in any way impairing the specific effect thereof.

The condensation products according to the invention are added to the rubber in such quantities that stabilisation against degradation by ozone is obtained. The appropriate quantities are known or may readily be determined by the average expert.

The new products are added to polychloroprene rubber for example in quantities of from 0.1 to 6.0% by weight and preferably in quantities of from 0.3 to 3.0% by weight, based on the polymer content which consists of 100.0% by weight of polychloroprene or of polychloroprene with a covulcanisable rubber, the minimum polychloroprene content amount to 20% by weight and preferably to 30% by weight.

Suitable rubbers covulcanisable with polychloroprene are, for example, natural rubbers or synthetic rubber-like polymers which still contain double bonds and which are obtained, for example, from conjugated diolefins, such as butadiene, dimethyl butadiene, isoprene and its homologs, or copolymers of such conjugated diolefins with polymerisable vinyl compounds, such as for example styrene, α-methyl styrene, acrylonitrile, methacrylonitrile, acrylates and methacrylates.

If the condensation products according to the invention are added to rubbers other than the above-mentioned polychloroprenes, they are best used in combination with waxes because a combination such as this has a synergistic effect.

The ratio by weight of wax to the condensation products according to the invention may vary within wide limits and is preferably between 0.25:1 and 2.5:1.

The waxes consist at least partly of microcrystalline paraffins. Macrocrystalline paraffins are paraffins of which the refractive index $n_D^{100}$ is lower than that calculated in accordance with the following equation:

$$n_D^{100} = 0.00035t + 1.4056 \text{ (t=solidification point in }°C.)$$

whilst microcrystalline paraffins are those of which the refractive index is higher than that calculated in accordance with the above equation (for a definition of petroleum waxes, see also Proceedings of ASTM-TAPPI Symposium on Petroleum Waxes, February 63, TAPPI-STAP No. 2, pages 1 to 19).

The following are examples of combinations of the cyclic acetals of diols according to the invention and waxes: 4 parts by weight of one of the condensation products mentioned as preferred at the beginning +2.0 parts by weight of microcrystalline paraffin.

Suitable rubbers are natural rubber or, in addition to polychloroprene, synthetic rubber-like polymers which still contain double bonds and which are obtained for example from conjugated diolefins, such as butadiene, dimethyl butadiene, isoprene and its homologs, or copolymers of such conjugated diolefins with polymerisable vinyl compounds, such as styrene, α-methyl styrene, acrylonitrile, methacrylonitrile, acrylates and methacrylates.

The synergistic anti-ozonant wax combination is added to the rubbers in such quantities that stabilisation against degradation by ozone is obtained. The appropriate quantities are known to or may readily be determined by the average expert. The quantities added range for example from 0.5 to 5% by weight and preferably from 1 to 10% by weight, based on the polymer content.

EXAMPLE 1

Preparation of the condensation product:

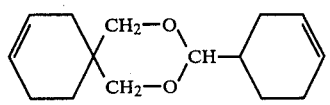

(a) 71 g (0.5 mol) of 1,1-dihydroxymethyl-Δ³-cyclohexene, 55 g (0.5 mol) of tetrahydro-Δ³-benzaldehyde and 3 g of p-toluene-sulphonic acid were boiled in 500 ml of toluene with water separation, until no more water was separated azeotropically. The toluene solution was stirred with 5 g of NaHCO₃ in order to neutralize the p-toluene-sulphonic acid. The mixture was filtered, the solution was freed from the solvent by distillation at 80° C./20 mbar. The remaining oil was distilled under a high vacuum.

Yield: 71.5 g=61% of theory of colourless oil b.p. 0.2 mbar/105°–110° C., $n_D^{20}$ 2.5109

(b) The same product was obtained in the following way: 142 g (1 mol) of 1,1-di-hydroxy-methyl-Δ³-cyclohexene, 110 g (1 mol) of tetrahydro-Δ³-benzaldehyde and 3 g of p-toluene-sulphonic acid were boiled in 400 ml of methanol for 8 hours with refluxing. After neutralisation and removal of the solvent an oil was obtained which was distilled under a high vacuum.

Yield: 174 g=74.4% of theory of colourless oil having the same boiling point and refractive index.

(c) The same product was also obtained by condensation of the components in water instead of methanol. The quantitative ratios of the components correspond to method (b). The yield was 61.5% of theory.

EXAMPLE 2

Preparation of

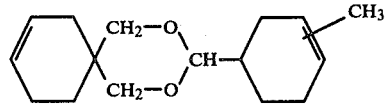

85.2 g (0.6 mol) of 1,1-di-hydroxymethyl-Δ³-cyclohexene, 78 g (0.6 mol) of 3- and 4-methyl-tetrahydro-Δ³-benzaldehyde and 3 g of p-toluene-sulphonic acid were boiled in 300 ml methanol for 8 hours with refluxing. The mixture was stirred with a solution of 6 g of NaHCO₃ in 300 ml of water, during which an oil was precipitated. This was separated off and distilled under a high vacuum.

Yield: 107 g=72% of theory of colourless oil b.p. 0.2 mbar/120°–125° C., $n_D^{20}$ 1.5098.

EXAMPLE 3

Preparation of

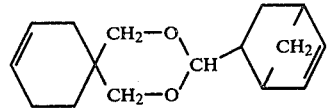

(a) 71 g (0.5 mol) of 1,1-di-hydroxymethyl-Δ³-cyclohexene, 61 g (0.5 mol) of 2,5-endomethylene-tetrahydro-Δ³-benzaldehyde and 1 g of p-toluene-sulphonic acid were boiled in 500 ml of cyclohexane with water separation, until no more water separates off azeotropically. The mixture was neutralised with 2 g of NaHCO₃, filtered and distilled at 80° C./20 mbar. The resulting oil was distilled under a high vacuum.

Yield: 77.6% of theory of colourless oil, b.p. 0.09 mbar/121° C., which solidified to colourless crystals having a melting point of 36°–38° C.

(b) The same product was obtained in a yield of 81.3% of theory by condensation of the components in methanol and (c) in a yield of 85.3% of theory by condensation in water. The quantitative proportions of the components are the same as in method (a).

EXAMPLE 4

Preparation of:

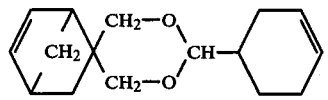

(a) 46.2 g (0.3 mol) of 1,1-di-hydroxymethyl-2,5-endomethylene-Δ³-cyclohexene, 34.8 g (0.3 mol) of tetrahydro-Δ³-benzaldehyde and 1 g of p-toluene-sulphonic acid were boiled in 200 ml of water for 5 hours with refluxing. The separated oil is taken up in methylene chloride and extracted with a solution of 2 g of NaHCO₃ in 200 ml of water. After separating off the methylene chloride solution and removing the solvent an oil remained which was distilled under a high vacuum.

Yield: 66 g=89% of theory of colourless oil b.p. 0.2 mbar/110° C., $n_D^{20}$ 1.5170.

(b) The same product was obtained by condensation of the components in toluene with a yield of 64% of theory. The quantitative proportions of the components used were the same as in method (a).

EXAMPLE 5

Preparation of:

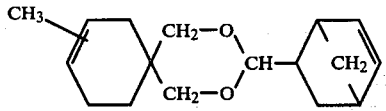

93.6 g (0.6 mol) of 1,1-di-hydroxymethyl-3- and 4-methyl-Δ³-cyclohexane, 73.2 g (0.6 mol) of 2,5-endomethylene-tetrahydro-Δ³-benzaldehyde and 3 g of p-toluene-sulphonic acid were boiled in 300 ml of toluene for 4 hours with water separation. For the purpose of neutralisation the mixture was stirred with 6 g of Ca(OH)₂ and filtered. After distilling off the toluene solution an oil remains which was distilled under a high vacuum.

Yield: 124 g=82.3% of theory of colourless oil b.p. 0.1 mbar/121° C., $n_D^{20}$ 1.5235.

EXAMPLE 6

Preparation of:

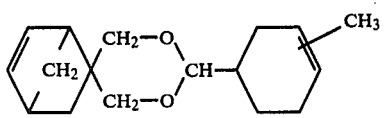

92.4 g (0.6 mol) of 1,1-di-hydroxymethyl-2,5-endomethylene-Δ³-cyclohexene, 78 g (0.6 mol) of 3- and 4-methyltetrahydro-Δ³-benzaldehyde and 3 g of p-toluene-sulphonic acid were boiled in 300 ml of methanol for 8 hours with refluxing. After neutralisation with 6 g of NaHCO₃ in 300 ml of water the separated oil was removed and distilled under a high vacuum.

Yield: 127 g=81.4% of theory of colourless oil b.p. 0.17 mbar/120°-125° C.

EXAMPLE 7

Preparation of:

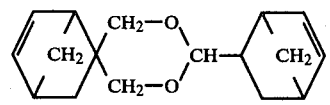

77 g (0.5 mol) of 1,1-hydroxymethyl-2,4-endomethylene-Δ³-cyclohexene, 77 g (0.5 mol) of 2,4-endomethylene-tetrahydro-Δ³-benzaldehyde and 2 g of p-toluene-sulphonic acid were boiled in 300 ml of water for 5 hours with refluxing. On cooling almost colourless crystals separated out. They were filtered and dried.

Yield: 120 g=93% of theory of slightly beige crystals m.p. 161°-162° C.

The same product was also obtained when carrying out the condensation reaction in methanol, toluene or cyclohexane.

EXAMPLE A

The following rubber mixture was prepared on a roller

| | |
|---|---|
| Polychloroprene | 100.0 parts by weight |
| magnesium oxide | 4.0 parts by weight |
| stearic acid | 0.5 parts by weight |
| precipitated silicic acid (BET surface area 180 m²/g) | 20.0 parts by weight |
| soft kaolin | 170.0 parts by weight |
| titanium dioxide | 5.0 parts by weight |
| antimony oxide | 5.0 parts by weight |
| naphthenic mineral oil softener | 20.0 parts by weight |
| chloroparaffin | 10.0 parts by weight |
| ethylene thiourea | 1.2 parts by weight |
| zinc oxide | 5.0 parts by weight |
| antiozonant | 0.5 parts by weight. |

Specimens of 0.4×4.5×4.5 cm and 0.4×4.5×5.5 were vulcanized (press vulcanization for 30 minutes at 150° C.) from these mixtures. 4 Specimens at a time were then stretched in a plastic frame such that surface elongations of 10, 20, 30 and 60% were produced. The stretched specimens were treated at room temperature with an air stream containing 1000 parts of ozone to 100 million parts of air. The samples were tested by eye for possible tears after 2, 4, 6, 8, 24, 48, 72, 96 and 168 hours. In the following tables the hours are recorded for the first time at which tears formed in each case. After 168 hours the tests were terminated.

TABLE 1

| | Elongation in % | | | |
|---|---|---|---|---|
| Product of example | 10 | 20 | 30 | 60 |
| without antioxonant (comparison) | 48 | 24 | 8 | 6 |
| 1 | >168 | >168 | >168 | >168 |
| 2 | >168 | >168 | >168 | 24 |
| 3 | >168 | >168 | >168 | >168 |
| 4 | >168 | >168 | >168 | >168 |
| 5 | >168 | >168 | >168 | >168 |
| 6 | >168 | >168 | >168 | 24 |
| 7 | >168 | >168 | >168 | >168 |

EXAMPLE B

The following rubber mixture was prepared on a roller:

| | |
|---|---|
| natural rubber | 100.0 parts by weight |
| zinc oxide | 10.0 parts by weight |
| precipitated chalk | 160.0 parts by weight |
| titanium dioxide | 10.0 parts by weight |
| stearic acid | 0.7 parts by weight |
| antiozonant wax | 2.0 parts by weight |
| dibenzothiazyl disulphide | 1.0 part by weight |
| hexamethylene tetramine | 0.25 parts by weight |
| sulphur | 2.2 parts by weight |
| antiozonant | 4.0 parts by weight |

The specimens were vulcanized in a press for 30 mins. at 140° C. The testing was carried out in the same way as in Example A, however, the ozone concentration was, instead of 1000 parts, 100 parts per 100 million parts of air.

TABLE 2

| Product according to Example | Elongation in % | | | |
|---|---|---|---|---|
| | 10 | 20 | 30 | 60 |
| without antioxonant (comparison) | 2 | 2 | 2 | 2 |
| 1 | 48 | 48 | 8 | 8 |
| 2 | >168 | >168 | 4 | 2 |
| 3 | 48 | 24 | 8 | 8 |
| 4 | >168 | 48 | 48 | 8 |
| 6 | >168 | >168 | 4 | 4 |
| 7 | >168 | >168 | 48 | 24 |

EXAMPLE C

The following mixture was prepared on a roller:

| | |
|---|---|
| styrene/butadiene copolymer | 100.0 parts by weight |
| zinc oxide | 5.0 parts by weight |
| carbon black (N220) | 55.0 parts by weight |
| naphthenic mineral oil softener | 2.0 parts by weight |
| highly aromatic mineral oil softener | 2.0 parts by weight |
| stearic acid | 2.0 parts by weight |
| antioxonant wax | 2.0 parts by weight |
| benzothiazyl-2-cyclohexyl-sulphenamide | 1.3 parts by weight |
| sulphur | 1.6 parts by weight |
| antiozonant | 4.0 parts by weight |

The specimens were vulcanized in a press for 30 mins. at 150° C. The testing was carried out in the same way as in Example A, however, the ozone concentration was, instead of 1000 parts, 100 parts per 100 million parts of air.

TABLE 3

| Product according to Example | Elongation in % | | | |
|---|---|---|---|---|
| | 10 | 20 | 30 | 60 |
| without antioxonant (comparison) | 4 | 2 | 2 | 2 |
| 1 | >168 | >168 | 4 | 2 |
| 3 | >168 | 6 | 4 | 2 |
| 4 | >168 | >168 | 6 | 2 |
| 7 | >168 | >168 | >168 | 2 |

EXAMPLE D

The following rubber mixture was prepared on a roll:

| | |
|---|---|
| styrene/butadiene copolymer | 50.0 parts by weight |
| natural rubber | 50.0 parts by weight |
| zinc oxide | 5.0 parts by weight |
| precipitated chalk | 120.0 parts by weight |
| precipitated silicic acid (BET surface area: 180 m²/g) | 35.0 parts by weight |
| diethylene glycol | 2.5 parts by weight |
| naphthenic mineral oil softener | 10.0 parts by weight |
| stearic acid | 1.0 parts by weight |
| antiozonant wax | 2.0 parts by weight |
| benzothiazyl-2-cyclohexylsulphenamide | 0.8 parts by weight |
| diphenyl guanidine | 0.3 parts by weight |
| tetramethylthiuran disulphide | 0.3 parts by weight |
| sulphur | 2.0 parts by weight |
| antiozonant | 4.0 parts by weight |

The specimens were vulcanized in a press for 15 mins. at 140° C. The testing was carried out in the same way as described in Example A, however, the ozone concentration was, instead of 1000 parts, 100 parts per 100 million parts of air.

TABLE 4

| Product according to Example | (NR/SBR) Elongation in % | | | |
|---|---|---|---|---|
| | 10 | 20 | 30 | 60 |
| without antiozonant (comparison) | 6 | 6 | 6 | 6 |
| 1 | 72 | 72 | 72 | 24 |
| 3 | >168 | 48 | 24 | 8 |
| 4 | >168 | 72 | 24 | 8 |
| 7 | >168 | 72 | 24 | 8 |

We claim:

1. A process for stabilizing a rubber against degradation under the effect of ozone, said rubber being selected from the group consisting of natural rubber, synthetic rubber and mixtures thereof and said process comprising adding to the rubber an antiozonant amount of a condensation product of a diol of the formula

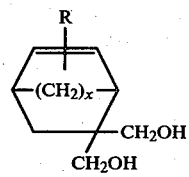

with an aldehyde of the formula

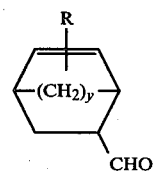

wherein R is hydrogen, 3-methyl or 4-methyl and x and y are independently either 0 or 1.

* * * * *